(12) United States Patent
Fukutani

(10) Patent No.: US 8,654,613 B2
(45) Date of Patent: Feb. 18, 2014

(54) MEASURING APPARATUS

(75) Inventor: Kazuhiko Fukutani, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 471 days.

(21) Appl. No.: 13/020,048

(22) Filed: Feb. 3, 2011

(65) Prior Publication Data

US 2011/0194380 A1 Aug. 11, 2011

(30) Foreign Application Priority Data

Feb. 9, 2010 (JP) ................................. 2010-026600
Jan. 20, 2011 (JP) ................................. 2011-009845

(51) Int. Cl.
*G01S 15/00* (2006.01)
*G01S 7/521* (2006.01)

(52) U.S. Cl.
CPC ..................... *G01S 7/521* (2013.01)
USPC ........................................................ 367/140

(58) Field of Classification Search
USPC ........................................................ 367/140
See application file for complete search history.

(56) References Cited

U.S. PATENT DOCUMENTS

| 6,607,489 | B2 | 8/2003 | Hoctor et al. ................. 600/443 |
| 7,864,307 | B2 | 1/2011 | Fukutani et al. ................ 356/73 |
| 2002/0173722 | A1* | 11/2002 | Hoctor et al. ................. 600/443 |
| 2006/0184042 | A1* | 8/2006 | Wang et al. .................. 600/476 |
| 2007/0236374 | A1* | 10/2007 | Brueske et al. ............... 341/143 |
| 2008/0306371 | A1 | 12/2008 | Fukutani et al. .............. 600/407 |
| 2009/0002685 | A1* | 1/2009 | Fukutani et al. ................ 356/72 |
| 2009/0005685 | A1* | 1/2009 | Nagae et al. .................. 600/459 |
| 2009/0198128 | A1 | 8/2009 | Fukutani et al. .............. 600/437 |
| 2010/0049049 | A1 | 2/2010 | Asao et al. .................... 600/443 |
| 2010/0053618 | A1 | 3/2010 | Nakajima et al. ............. 356/432 |
| 2010/0087733 | A1 | 4/2010 | Nakajima et al. ............. 600/437 |
| 2010/0191109 | A1 | 7/2010 | Fukutani et al. .............. 600/437 |
| 2010/0331662 | A1 | 12/2010 | Fukutani et al. .............. 600/407 |
| 2011/0128816 | A1 | 6/2011 | Baba et al. ...................... 367/11 |

FOREIGN PATENT DOCUMENTS

JP 2006-208050 8/2006

* cited by examiner

*Primary Examiner* — Isam Alsomiri
*Assistant Examiner* — James Hulka
(74) *Attorney, Agent, or Firm* — Fitzpatrick, Cella, Harper & Scinto

(57) ABSTRACT

A measuring apparatus includes an acoustic wave detecting unit that detects acoustic waves generated from a subject irradiated with light, and a member that is disposed between the acoustic wave detecting unit and the subject and that has an acoustic speed value smaller than an average acoustic speed value inside the subject. The thickness of the member is greater than a value obtained by dividing the acoustic speed value inside the subject by the minimum frequency detectable by the acoustic wave detecting unit.

6 Claims, 4 Drawing Sheets

MEASURING APPARATUS

BACKGROUND OF THE INVENTION

1. Field of the Invention

The invention relates to a measuring apparatus.

2. Description of the Related Art

In general, imaging apparatus using X-rays, ultrasonic waves, or nuclear magnetic resonance imaging technique (MRI) are used commonly in the medical field. On the other hand, study has been pursued actively on an optical imaging apparatus that acquires in-vivo information by propagating, through a living subject, light, such as laser light, from a light source and with which a living body has been irradiated, and detecting the propagated light. An example of an optical imaging technique includes photoacoustic tomography (PAT).

In PAT, a subject is irradiated with pulsed light that is generated from a light source to detect temporal variations in acoustic waves (typically, ultrasonic waves) generated from living tissue which has absorbed the energy of the light propagated and diffused inside the subject at a plurality of portions surrounding the subject. Then, the information regarding the optical characteristic values of the subject is visualized through a process of mathematically analyzing the detected signals. Thus, since it is possible to obtain an initial pressure generation distribution or a light energy absorption density distribution generated when the subject is irradiated with light, the position of a malignant tumor caused due to new vascular reproduction can be designated. The term "photoacoustic imaging apparatus" herein refers to an imaging apparatus that uses the PAT technique.

In general, in PAT, there is a closed surface (particularly, many points on a spherical measurement surface) surrounding or enclosing the entire subject. Therefore, it is desirable to measure a temporal variation in acoustic waves using an ideal acoustic wave detecting unit (broad-band and point detection). By performing processing using an image reconstruction method based on the measured result, an initial acoustic pressure distribution generated by light irradiation can completely be visualized in theory.

U.S. Pat. No. 6,607,489 discloses correction in image reconstruction.

SUMMARY OF THE INVENTION

According to general image reconstruction theory, it is assumed that the acoustic wave detecting unit detecting photo-acoustic waves performs point detection (that is, detects information at exactly a point having no size). In effect, since the acoustic wave detecting unit has a finite size, however, the angle of the acoustic wave received by the finite size is restricted. The sensitivity ratio of an acoustic wave (an angle of this line is assumed to be 0) vertically incident on the acoustic wave detecting unit to an acoustic wave incident at angle $\theta$ with respect to the vertical can be expressed by Expression (1) below (these acoustic waves enter the acoustic wave detecting unit at same strength):

[Expression 1]

$$R_\theta = \left| \frac{\sin(k \cdot d_e \sin\theta)}{k \cdot d_e \sin\theta} \right| \quad (1)$$

In this Expression, $k=2\pi/\lambda$, $d_e$ is the detection width (pitch) of the acoustic wave detecting unit, and $\lambda$ is the wavelength of the incident acoustic wave. From this expression, it can be understood that as the detection width $d_e$ of the acoustic wave detecting unit is increased, the sensitivity of an acoustic wave incident at a large angle with respect to a direction perpendicular to the surface of the acoustic wave detecting unit is lowered. The characteristic of the acoustic wave detecting unit is called its directivity. It is said that the smaller the detectable angle is, the higher the directivity is. That is, if the detection width of the acoustic wave detecting unit is increased, the directivity becomes higher.

From this theory, in order to be suitable for the image reconstruction theory, it is desirable to use an acoustic wave detecting unit capable of acquiring a signal of a wide range and having low directivity (having the narrow detection width) in PAT.

On the other hand, in order to improve element sensitivity when detecting acoustic waves, it is desirable that the detection width is large. Expression (2) indicating the relationship of the element sensitivity is shown:

[Expression 2]

$$P_{min} = \sqrt{\frac{9.2\,kT \cdot f_{max}}{c_l \varepsilon \varepsilon_0 g_{33}^2 A}} \propto \sqrt{\frac{1}{A}} = d^{-1} \quad (2)$$

In this expression, $P_{min}$ denotes the minimum detection acoustic pressure. As the value of the detection acoustic pressure becomes smaller, acoustic waves with even a small acoustic pressure can be detected sensitively without being hidden by noise. In this expression, k is the Boltzmann constant, t is temperature, $c_1$ is the acoustic speed in a material of the detecting unit, $\varepsilon$ is a dielectric constant of the material of the detection unit, $\varepsilon_0$ is the dielectric constant of vacuum, and $g_{33}$ is a piezoelectric constant, and the values thereof are all determined depending on the material of the detecting unit. $f_{max}$ is a maximum measuring frequency of the detecting unit, and A is the detection width of a probe. For a given value of $f_{max}$, the minimum detection acoustic pressure becomes smaller with an increase in the subsequent detection width A, thereby permitting detection of a small acoustic pressure. That is, if the detection width A is narrowed to lower the directivity, the minimum detection acoustic pressure becomes larger.

The invention is realized in view of the above-mentioned circumstance, and an object of the invention is to provide a measuring apparatus capable of detecting acoustic waves with high sensitivity, and acquiring a signal over a wide range.

A measuring apparatus according to this invention may comprise an acoustic wave detecting unit that detects acoustic waves generated from a subject irradiated with light, and a member that is disposed between the acoustic wave detecting unit and the subject and has an acoustic speed value smaller than an average acoustic speed value inside the subject, where the thickness of the member is greater than a value obtained by dividing the acoustic speed value inside the subject by the minimum frequency detectable by the acoustic wave detecting unit.

In such a measurement apparatus, it is possible to detect an acoustic wave of high sensitivity and to acquire a signal over a wide range.

Further features of the present invention will become apparent from the following description of exemplary embodiments with reference to the attached drawings.

DESCRIPTION OF THE EMBODIMENTS

Hereinafter, an embodiment of the invention will be described with reference to the drawings. The purpose of the measuring apparatus (photoacoustic imaging apparatus) described herein is to diagnose a malignant tumor or vascular disease or to observe the progress of chemical treatment. It is possible to perform imaging of the subject information. The subject information is a distribution of a generation source of acoustic waves (photoacoustic waves) generated by light irradiation, an initial pressure distribution inside a subject or a density distribution of light energy absorption of guided light, and a density distribution of a material forming a subject tissue obtained from the information. Examples of the density distribution of a material include oxygen saturation and oxidation-reduction hemoglobin concentration.

Figure 1:
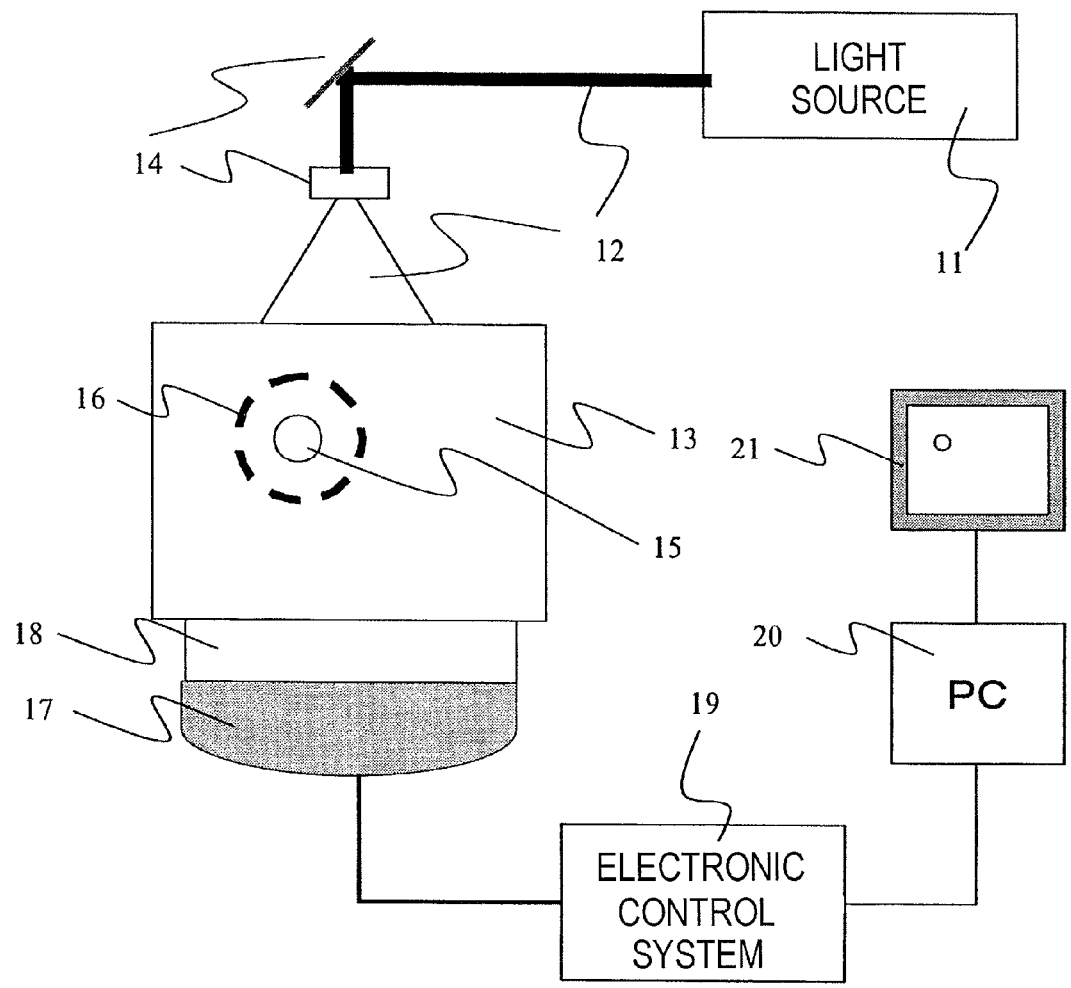
FIG. 1 is a schematic diagram illustrating an example of the configuration of a measuring apparatus.

FIG. 1 is a diagram illustrating a photoacoustic imaging apparatus according to an embodiment of the invention. The photoacoustic imaging apparatus includes a light source 11 irradiating a subject 13 with light 12 emitted from the light source 11 and an optical unit 14, such as a lens, guiding the light 12 to the subject 13. The photoacoustic imaging apparatus also includes an acoustic wave detecting unit 17 detecting acoustic waves 16 generated by a light absorber 15 such as blood inside the subject 13 absorbing a part of the energy of the light 12, and a low acoustic speed member 18 changing an incident angle of the acoustic waves 16 incident on the acoustic wave detecting unit 17. The low acoustic speed member 18 is preferably a sheet-shaped member. The photoacoustic imaging apparatus also includes an electronic control system 19 performing amplification, digital conversion, or the like on the electric signal, a signal processing unit 20 forming an image (that is, generating image data) based on the subject information, and a display unit 21 displaying the formed image. In this embodiment, a personal computer (PC) is used as the signal processing unit 20. A display or the like is used as the display unit.

Pulses with continuously varying energy are used as the light 12 irradiated to the subject 13. Then, the thermal expansion results in generating the acoustic waves 16 from the light absorber 15 present inside the subject. This is because the absorber absorbs the pulsed light, so that the temperature of the absorber increases, a volume expansion is caused by the temperature increase, and thus acoustic waves 16 are generated. It is desirable that the time duration of the light pulses satisfies the heat-stress confinement condition in order to efficiently confine the energy absorbed by the light absorber 15. Typically, the time duration is in the range from several nanoseconds to several tens of nanoseconds. The acoustic wave detecting unit 17 detects the generated acoustic waves 16 via the low acoustic speed member 18 and the electronic control system 19 processes the detected electric signals. The signal processing unit 20 converts the electric signals into subject information image data and displays the subject information image data on the display unit 21.

Figure 2:
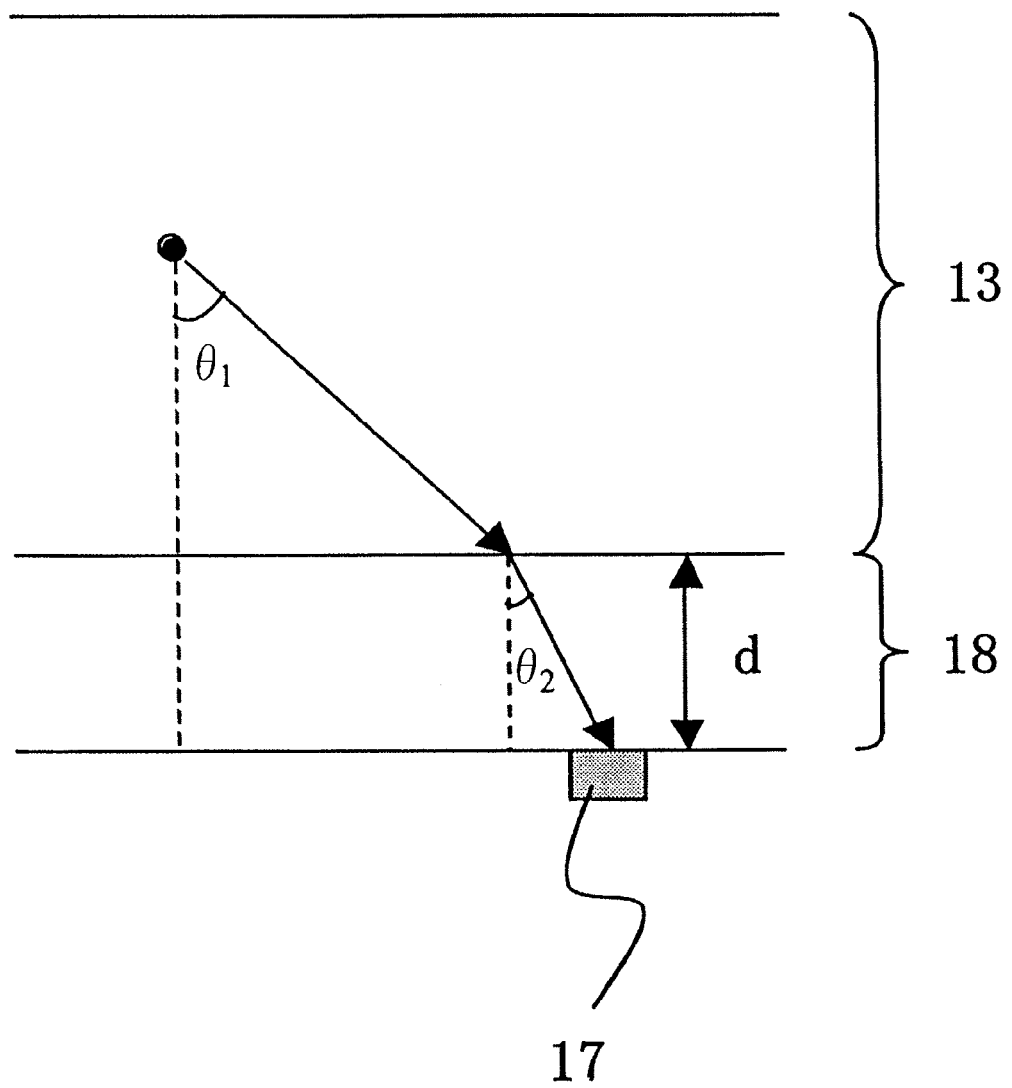
FIG. 2 is a schematic diagram illustrating an example of the advantage of a low acoustic speed member.

Next, the effects of the low acoustic speed member 18 according to the invention will be described in detail with reference to FIG. 2. FIG. 2 is a diagram illustrating an example of disposition of the subject 13, the acoustic wave detecting unit 17, and the low acoustic speed member 18. According to the invention, the low acoustic speed member 18 is disposed between the subject 13 and the acoustic wave detecting unit 17. Although not illustrated, another material may be inserted between the subject 13 and the low acoustic speed member 18 and between the low acoustic speed member 18 and the acoustic wave detecting unit 17 to achieve acoustic impedance matching. However, the material is preferably as thin as possible. On the assumption that $v_2$ is a propagation speed (acoustic speed value inside the low acoustic speed member) of the acoustic waves inside the low acoustic speed member and $v_1$ is an average propagation speed (average acoustic speed value inside the subject) of the acoustic waves inside the subject, the relation $v_1 > v_2$ has to be satisfied. The reason for satisfying this relation will be described below. The acoustic impedance value of the low acoustic speed member 18 is preferably close to the acoustic impedance value of the subject 13, when the acoustic impedance matching material is not inserted between the subject 13 and the low acoustic speed member 18. The reason is because when a difference between the acoustic impedances is large, a part of the acoustic waves 16 incident on the low acoustic speed member 18 from the subject 13 is reflected.

The thickness d of the low acoustic speed member 18 is preferably greater than a value obtained by dividing the acoustic speed $v_2$ of the low acoustic speed member 18 by the minimum frequency $f_{min}$ detectable by the acoustic wave detecting unit 17 ($d > v_2/f_{min}$). Here, the minimum frequency $f_{min}$ detectable by the acoustic wave detecting unit 17 is typically a frequency detected with half sensitivity with respect to a frequency $f_c$ of the maximum frequency. The reason is that when the thickness of the low acoustic speed member 18 is not greater than the wavelength of the detected acoustic waves 16, no refraction occurs due to a difference in the acoustic speed. In concrete numbers, the minimum thickness d of the low acoustic speed member is 2 mm, when the low acoustic speed member is made of silicon rubber (acoustic speed is lower than 1000 m/sec) and the minimum frequency detectable by the acoustic wave detecting unit is 0.5 MHz.

When the thickness of the low acoustic speed member 18 satisfies the above condition, an angle $\theta_1$ of the acoustic wave 16 incident on the low acoustic speed member 18 from the subject and an angle $\theta_2$ of the acoustic wave 16 incident on the acoustic wave detecting unit 17 from the low acoustic speed member 18 are determined by Snell's law expressed in Expression (3) below. Therefore, when the acoustic speed $v_2$ of the low acoustic speed member 18 is slower than the acoustic speed $v_1$ of the subject 13, the angle $\theta_2$ of the acoustic wave 16 incident on the acoustic wave detecting unit 17 from the low acoustic speed member 18 is smaller than the angle $\theta_1$ of the acoustic wave 16 incident on the low acoustic speed member 18 from the subject 13. That is, when no low acoustic speed member is provided, the acoustic wave 16 incident on the acoustic wave detecting unit 17 at an angle (for example, $\theta_1$) that makes the signal difficult to detect due to directivity also enters the low acoustic speed member 18, so that the acoustic wave 16 is refracted due to a difference in the acoustic speed and the incident angle (for example, $\theta_2$) varies. Thus, since the detecting unit has large sensitivity, the acoustic waves can also be detected at an angle at which the acoustic waves may not be detected in the related art.

$$v_1/v_2 = \sin\theta_1/\sin\theta_2 \qquad (3)$$

Moreover, in order to suppress attenuation of the acoustic wave in the low acoustic speed member, the maximum thickness d of the low acoustic wave member is preferably one which limits the attenuation in the low acoustic speed member to 20 dB or less, and more preferably, to 10 dB or less. For example, the maximum thickness $d_{max}$ of the low acoustic speed member is as follows: $d_{max}=A/(f_{max}\times\alpha)$, when the admissible attenuation of the low acoustic speed member is A, frequency dependence attenuation coefficient of the low acoustic speed member is $\alpha$ (dB/MHz·cm), and the maximum frequency detectable by the acoustic wave detecting unit 17 is $f_{max}$.

The maximum frequency $f_{max}$ detectable by the acoustic wave detecting unit 17 notes, typically, the maximum frequency detected with half sensitivity with respect to the frequency $f_c$ detectable with the maximum sensitivity. By setting the thickness of the low acoustic speed member below such thickness, attenuation of the acoustic wave can be suppressed. In concrete numbers, the maximum thickness d of the low acoustic speed member is 10 mm, when the low acoustic speed member is silicon rubber (attenuation rate: 1.0 dB/MHz·cm), admissible attenuation is 20 dB, and the maximum frequency detectable with the acoustic wave detecting unit is 2 MHz. Even if other material is used as the low acoustic speed member, the preferable thickness of the low acoustic speed member is 10 mm or less. More preferably, the thickness of the low acoustic speed member is 8 mm or less, and 5 mm or less is most preferable.

The low acoustic speed member 18 may have an acoustic speed slower than the average acoustic speed of the subject 13. When the subject 13 is a living body, the average acoustic speed is up to 1530 m/second. A liquid such as heavy water (up to 1381 m/second), ethyl alcohol (up to 1207 m/second), or methyl alcohol (up to 1103 m/second) with an acoustic speed slower than this average acoustic speed, rubber such as silicon rubber (up to 1000 m/second), or the like can be used. That is, a hard material such as an inorganic material may not be used, and a relatively soft material is preferable. Since the material can be changed flexibly depending on the shape of the subject 13, it is possible to suppress a factor, such as a void between the subject 13 and the low acoustic speed member 18, which could cause deterioration in the propagation of the acoustic waves.

Figure 3:
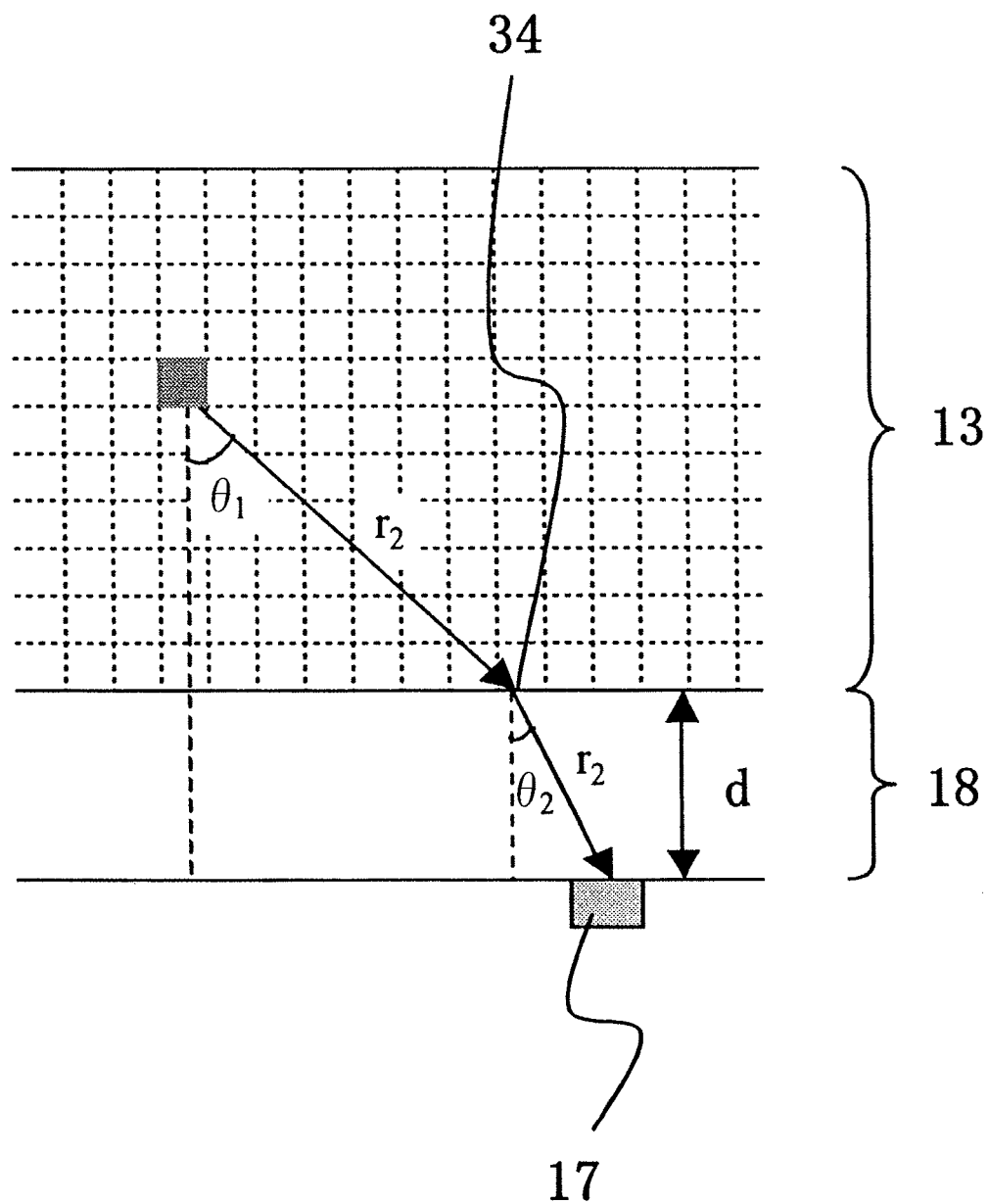
FIG. 3 is a schematic diagram illustrating an example of an image reconstruction method.

Next, exemplary processing performed by the signal processing apparatus according to the invention will be described with reference to FIG. 3. In FIG. 3, reference numerals 13, 18, 17 and 34 denote a subject, a low acoustic speed member, an acoustic wave detecting unit, and a refraction point of an acoustic wave, respectively. In an image reconstruction process, the area of the subject 13 to be imaged is first discretized, that is, divided into smaller areas. When a 3-dimensional image is formed, the area is divided into voxels. When a 2-dimensional image is formed, as shown in FIG. 3, the area is divided into pixels. In a normal image reconstruction process, the distance between a pixel (voxel or pixel) of interest and a detection point is determined and a value added to the pixel of interest is determined from the formed angle. In this embodiment, however, since the acoustic waves are refracted on the interface (here, the refraction point 34) between the low acoustic speed member 18 and the subject 13, the propagation distance of the acoustic waves varies. Therefore, the position of the refraction point is calculated from the geometric shape, and the propagation distance (here, $r_1+r_2$) of the acoustic wave from the pixel of interest to the detecting unit is calculated. Moreover, the angle $\theta_2$ is calculated and the value added to the pixel of interest is calculated from the value of this angle. By performing this process, an image distorted due to the acoustic speed of the low acoustic speed member 18 can be corrected with high precision.

Next, this embodiment will be described in detail.

In FIG. 1, the light source 11 irradiates the subject 13 with the light 12 having a wavelength absorbed by a specific component among the components forming the subject 13. The light source 11 may be disposed to be integrated with the photoacoustic imaging apparatus or may be disposed to be separated from the apparatus.

The light source 11 includes at least one of pulse light sources capable of emitting several-nanosecond order pulsed light to several hundreds-of-nanosecond order pulsed light. When the detected acoustic waves have a small acoustic pressure, the above order pulsed light may not be used, but light, such as a sine wave, with temporally varying intensity may be used. In this embodiment, only one source is used as the light source 11, but a plurality of light sources may be used. In this case, a plurality of light sources having the same wavelength may be used to improve the intensity of the light with which the subject 13 is irradiated. Alternatively, a plurality of light sources with different oscillation wavelengths may be used, to measure a difference in an optical characteristic value distribution caused due to the wavelengths.

A laser capable of releasing large output is preferably used as the light source 11, but a light-emitting diode or the like may be used instead of a laser. Examples of the laser include a solid-state laser, a gas laser, a dye laser, and a semiconductor laser. When dye, optical parametric oscillators (OPO), or titanium sapphire and alexandrite crystals through which the oscillated wavelengths are converted may be used as the light source 11, the difference in the optical characteristic value distribution caused due to the wavelengths can be measured.

The wavelength of the light source to be used is preferably in the range from 700 nm to 1100 nm, in which the light is less absorbed inside the subject. However, when the optical characteristic value distribution of a subject tissue near the surface of the subject is required, a wavelength range, for example, from 400 nm to 1600 nm which is broader than the above wavelength area may be used.

In FIG. 1, the light 12 emitted from the light source 11 can be propagated using a light waveguide. Although not illustrated in FIG. 1, an optical fiber is preferably used as such a light waveguide. When an optical fiber is used, a plurality of optical fibers is used for the light sources, respectively, to guide the light toward the surface of the subject. Alternatively, the light from the plurality of light sources may be guided to one optical fiber and all the light may be guided toward the subject 13 through that one optical fiber.

The optical unit 14 in FIG. 1 refers to a mirror that mainly reflects the light 12 or a lens changing the form of the light by collecting or expanding the light 12. Any optical component may be used as the optical unit 14, as long as the optical component irradiates the subject 13 with a desired form of the light 12 emitted from the light source 11. In general, enlarging an area of the light 12 to some extent is more preferable than collecting the light 12 using a lens. The area of the subject 13 irradiated with the light 12 is preferably controllable. In other words, in the photoacoustic imaging apparatus according to the invention, the light 12 emitted from the light source 11 is preferably movable on the subject. When the light 12 is movable, the light 12 can be emitted more broadly. The area (the light 12 irradiated to the subject 13) of the subject 13 irradiated with the light 12 is preferably moved in synchronization with the acoustic wave detecting unit 17. As a method of moving the area of the subject 13 irradiated with the light 12, the above-described mirrors are to move, and the irradiated area may be moved or the light source itself may mechanically be moved.

The breast, the finger, hand and foot, or the like of a human or an animal may be examined as the subject 13 to diagnose malignant tumors or vascular disease of the human or animal or observe progress of chemical treatment. An absorber with a high absorption coefficient inside the subject is used as the light absorber 15 of the subject 13. For example, when a human body is a measurement target, oxygenated hemoglobin or deoxygenated hemoglobin, a blood vessel containing oxygenated hemoglobin or deoxygenated hemoglobin, or a malignant tumor including many new blood vessels is examined. A contrast agent introduced from the outside of the subject 13 may be used as the light absorber 15.

The acoustic wave detecting unit 17 in FIG. 1 detects the acoustic waves 16 generated from the light absorber 15 and converts the acoustic waves into electric signals. Any unit, such as a transducer using piezoelectric phenomenon, a transducer using resonance of light, or a transducer using variation in volume, capable of detecting the acoustic waves may be suitably used as the acoustic wave detecting unit.

A unit having a plurality of detecting elements arranged two-dimensionally may be used as the acoustic wave detecting unit. When the two-dimensionally arranged elements are used, it is possible to simultaneously detect the acoustic waves at a plurality of positions, thereby shortening the detection time and reducing the influence of the vibration of the subject. At this time, the "detection width $d_e$" (pitch) refers to the width of one element.

The low acoustic speed member 18 in FIG. 1 adjusts the incident angle of the acoustic waves 16 incident on the acoustic wave detecting unit 17, as described above. When the acoustic speed value of the low acoustic speed member 18 is smaller than the average acoustic speed value of the subject 13, any material may be used. Typically, a soft material such as a liquid or rubber is used. The material has an advantage that the shape can easily be modified depending on the shape of the subject 13. When a liquid is used, the liquid is preferably kept in a bag-like body or a container made of plastic. When rubber is used, the rubber can be used without being kept. Although not illustrated, an acoustic impedance matching agent such as gel may be used between the low acoustic speed member 18 and the subject 13 and between the low acoustic speed member 18 and the acoustic wave detecting unit 17 in order to prevent reflection of the acoustic waves 16. The low acoustic speed member 18 may be formed of a sheet-shaped member with a homogeneous and uniform thickness. That is, the thickness d of the low acoustic speed member 18 may be constant in the entire area and the sheet may be formed of a uniform material. Then, when the acoustic wave detecting unit 17 is formed by the two-dimensionally arranged elements, it is not necessary to dispose the low acoustic speed member 18 for each element. Moreover, an incident angle or a distance can be easily calculated when the acoustic waves are refracted.

The electronic control system 19 in FIG. 1 amplifies the electric signals obtained from the acoustic wave detecting unit 17 and converts the analog signals into the digital signals. The signal processing unit 20 stores the measured data obtained from the electronic control system and an arithmetic unit converts the measured data into image data (volume data) of an optical characteristic value distribution. A PC or the like analyzing various kinds of data can be used as the signal processing unit. A time domain method such as a universal back projection used in a normal PAT, a Fourier domain method, or the like may be used as a method (image reconstruction method) of generating image data. By correcting the reconstructed image in consideration of the low acoustic speed member 18, it is possible to form an image with more precision. Any image display unit capable of displaying the image data generated by the signal processing unit 20 can be used as the image display unit 21 in FIG. 1. For example, a liquid crystal display or the like can be used.

By using the photoacoustic imaging apparatus using the low acoustic speed member 18 satisfying the above-described conditions, as described above, the photoacoustic waves incident at a larger angle can be detected even when the detection width of the acoustic wave detecting unit 17 is set to be large. Therefore, an image for more precise diagnosis can be formed. That is, it is possible not only to detect the acoustic wave of high sensitivity but also to acquire a signal of a wide range by the acoustic wave detecting unit 17 realizing the wide detection width.

When light with a plurality of wavelengths is used in the light source 11, an absorption coefficient distribution inside a subject is calculated for each wavelength by the above system. By comparing the value of the absorption coefficient distribution to a wavelength dependency unique to a material (glucose, collagen, oxygenated/deoxygenated hemoglobin, or the like) forming a tissue of the subject, a density distribution of the material forming the subject 13 can also be imaged.

Modification Example

Figure 4:
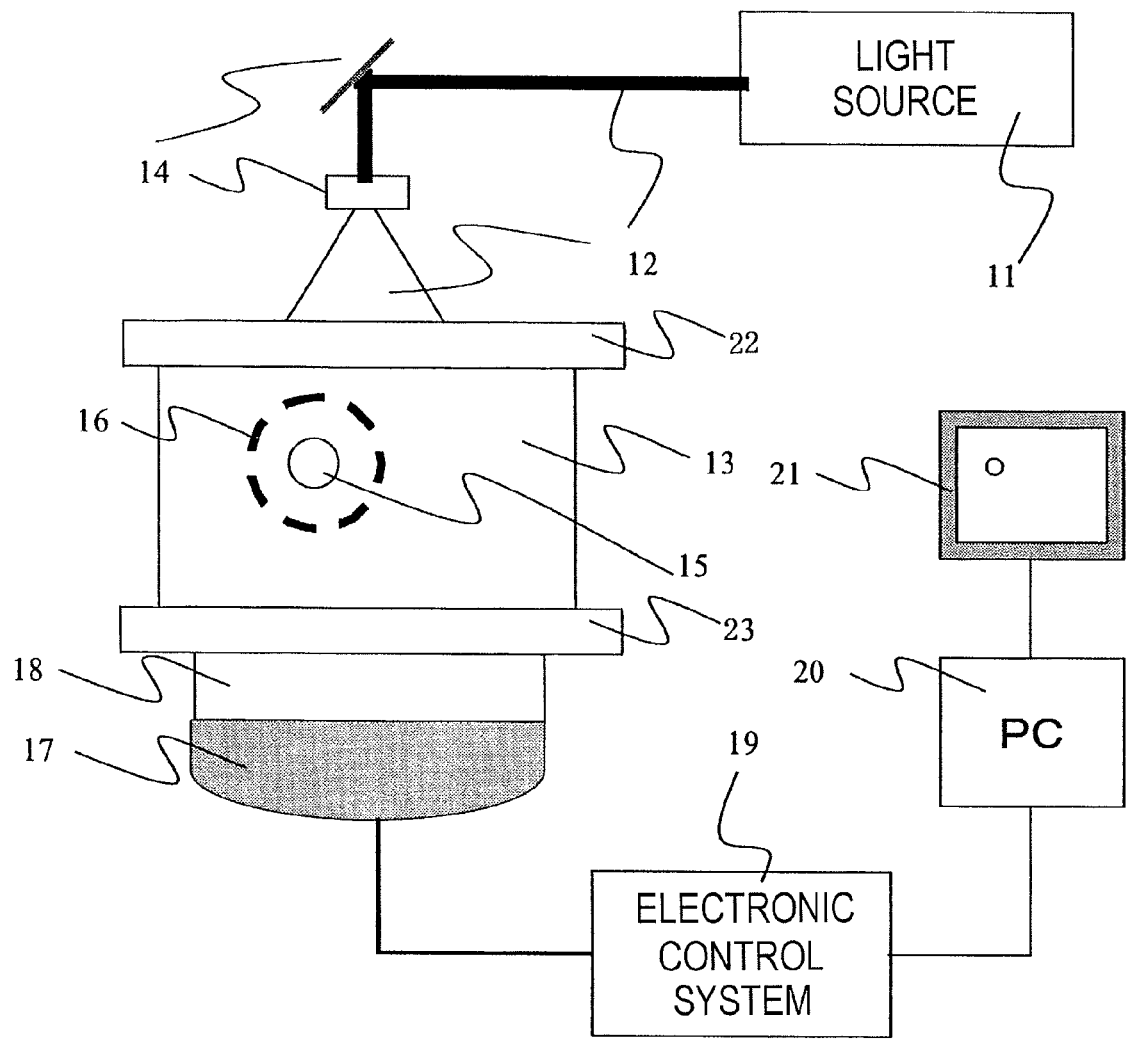
FIG. 4 is a schematic diagram illustrating the configuration of a measuring apparatus according to a modification example.

Next, a modification example in which the configuration of the measuring apparatus (photoacoustic imaging apparatus) is partially modified will be described. FIG. 4 is a block diagram illustrating the configuration of the measuring apparatus according to the modification example. This measuring apparatus is different from that in FIG. 1 in that the subject 13 is oppressed between a first holding plate 22 and a second holding plate 23. A flat plate having high transparency and low attenuation characteristic for the light 12 from the light source 11 is used as the first holding plate 22. A flat plate having high transparency and low attenuation characteristic for the acoustic wave is used as the second holding plate 23. The movement of the subject 13 can be suppressed and held by the two holding plates.

The low acoustic speed member 18 is disposed between the second holding plate 23 and the acoustic wave detecting unit 17. Then, as in the above embodiment, it is possible to obtain the advantages that not only the acoustic wave of high sensitivity is detected but also a signal of a wide range is acquired. A material for acoustic impedance matching may be inserted between the second holding plate 23 and the subject 13 or the low acoustic speed member 18, if necessary.

In particular, when a sheet-shaped material is used as the low acoustic speed member, only the sheet may be attached to the second holding plate 23. Therefore, the measuring apparatus can easily be configured.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-026600, filed on Feb. 9, 2010, and Japanese Patent Application No. 2011-009845, filed on Jan. 20, 2011, which are hereby incorporated by reference herein in their entirety.

What is claimed is:

1. A measuring apparatus comprising:
   an acoustic wave detecting unit that detects acoustic waves generated from a subject irradiated with light; and
   a member that is disposed between said acoustic wave detecting unit and the subject and has an acoustic speed value smaller than an average acoustic speed value inside the subject,
   wherein a thickness of said member is greater than a value obtained by dividing the acoustic speed value inside the subject by the minimum frequency detectable by said acoustic wave detecting unit and is greater than a wavelength of the acoustic wave.

2. The measuring apparatus according to claim 1, wherein the minimum frequency detectable by said acoustic wave detecting unit is a frequency detected with half sensitivity with respect to a frequency detectable with the maximum sensitivity of said acoustic wave detecting unit.

3. The measuring apparatus according to claim 1, further comprising a signal processing unit that acquires a subject information based on the detected acoustic waves, wherein, when determining a generated location of the acoustic waves, said signal processing unit acquires the subject information by calculating a distance up to the generated location of the acoustic waves based on a variation in an incident angle of the acoustic waves on said acoustic wave detecting unit according to a ratio of the acoustic speed value inside said member to the average acoustic speed value inside the subject.

4. The measuring apparatus according to claim 1, further comprising:
   a first holding plate; and
   a second holding plate that holds the subject together with said first holding plate between said member and the subject, wherein said member is disposed on said second holding plate.

5. The measuring apparatus according to claim 1, wherein said member has a sheet-like shape.

6. The measuring apparatus according to claim 1, wherein the shape of said member is varied depending on the shape of the subject.

* * * * *